United States Patent
Roberts et al.

(10) Patent No.: US 11,806,898 B2
(45) Date of Patent: Nov. 7, 2023

(54) METHODS FOR INCREASING A RETENTION FORCE BETWEEN A POLYMERIC SCAFFOLD AND A DELIVERY BALLOON

(71) Applicant: Abbott Cardiovascular Systems Inc., Santa Clara, CA (US)

(72) Inventors: Lily Ayo Roberts, San Francisco, CA (US); Sean A. McNiven, San Francisco, CA (US); Kathleen Yan, Cupertino, CA (US); Boyd V. Knott, Menifee, CA (US); Jeremy B. Beer, Mountain View, CA (US); Mark C. Johnson, Murrieta, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 17/834,872

(22) Filed: Jun. 7, 2022

(65) Prior Publication Data
US 2022/0297351 A1  Sep. 22, 2022

Related U.S. Application Data

(63) Continuation of application No. 16/102,384, filed on Aug. 13, 2018, now Pat. No. 11,376,762, which is a
(Continued)

(51) Int. Cl.
*A61F 2/958* (2013.01)
*B29B 11/04* (2006.01)
(Continued)

(52) U.S. Cl.
CPC .............. *B29B 11/04* (2013.01); *A61F 2/915* (2013.01); *A61F 2/958* (2013.01); *A61F 2/9524* (2020.05);
(Continued)

(58) Field of Classification Search
CPC .............................. A61F 2/9524; A61F 2/958
See application file for complete search history.

(56) References Cited

U.S. PATENT DOCUMENTS 5,836,965 A  11/1998  Jendersee et al.
5,913,871 A   6/1999  Werneth et al.
(Continued)

FOREIGN PATENT DOCUMENTS

CA   2 526 038   5/2006
EP   0 787 020   8/1997
(Continued)

OTHER PUBLICATIONS

International Search Report and Written Opinion dated Aug. 9, 2012 in International Patent Application No. PCT/US2012/033955, 12 pages.
(Continued)

*Primary Examiner* — Jeffry H Aftergut
(74) *Attorney, Agent, or Firm* — Squire Patton Boggs (US) LLP

(57) ABSTRACT

A medical device includes a scaffold crimped to a catheter having an expansion balloon. The scaffold is crimped to the balloon by a process that includes inflating the delivery balloon during a diameter reduction to improve scaffold retention and maintaining an inflated balloon during the diameter reduction and prior and subsequent dwell periods.

8 Claims, 3 Drawing Sheets

Related U.S. Application Data continuation of application No. 14/535,246, filed on Nov. 6, 2014, now Pat. No. 10,059,034, which is a continuation of application No. 13/089,225, filed on Apr. 18, 2011, now Pat. No. 8,961,848.

(51) Int. Cl.

| | | |
|---|---|---|
| *B29C 65/66* | (2006.01) | |
| *B29C 65/00* | (2006.01) | |
| *B29C 67/00* | (2017.01) | |
| *B29C 65/78* | (2006.01) | |
| *A61F 2/915* | (2013.01) | |
| *A61F 2/95* | (2013.01) | |
| *A61L 31/00* | (2006.01) | |
| *B29L 31/00* | (2006.01) | |
| *B29L 28/00* | (2006.01) | |
| *B29C 55/24* | (2006.01) | |
| *B29K 101/00* | (2006.01) | |

(52) U.S. Cl.
CPC .............. *A61L 31/00* (2013.01); *B29C 65/66* (2013.01); *B29C 65/7817* (2013.01); *B29C 66/532* (2013.01); *B29C 66/63* (2013.01); *B29C 66/71* (2013.01); *B29C 66/73117* (2013.01); *B29C 66/73791* (2013.01); *B29C 66/91411* (2013.01); *B29C 66/91945* (2013.01); *B29C 66/9292* (2013.01); *B29C 66/92445* (2013.01); *B29C 66/92921* (2013.01); *B29C 67/0014* (2013.01); *A61F 2/9522* (2020.05); *A61F 2002/9583* (2013.01); *A61F 2250/0067* (2013.01); *B29C 55/24* (2013.01); *B29C 66/91421* (2013.01); *B29C 66/949* (2013.01); *B29C 2793/0009* (2013.01); *B29K 2101/00* (2013.01); *B29L 2028/00* (2013.01); *B29L 2031/7534* (2013.01); *B29L 2031/7543* (2013.01)

(56) References Cited

U.S. PATENT DOCUMENTS

| | | | |
|---|---|---|---|
| 5,976,181 A | 11/1999 | Whelan et al. | |
| 6,063,092 A | 5/2000 | Shin | |
| 6,629,350 B2 | 10/2003 | Motsenbocker | |
| 6,666,880 B1 | 12/2003 | Chiu et al. | |
| 6,745,445 B2 | 6/2004 | Spilka | |
| 6,863,683 B2 | 3/2005 | Schwager et al. | |
| 7,010,850 B2 | 3/2006 | Hijlkema et al. | |
| 7,316,148 B2 | 1/2008 | Asmus et al. | |
| 7,761,968 B2 | 7/2010 | Huang et al. | |
| 7,951,185 B1 | 5/2011 | Abbate et al. | |
| 8,002,817 B2 | 8/2011 | Limon | |
| 8,046,897 B2 | 11/2011 | Wang et al. | |
| 8,062,465 B1 | 11/2011 | Huang et al. | |
| 8,123,793 B2 | 2/2012 | Roach et al. | |
| 8,261,423 B2 | 9/2012 | Jow et al. | |
| 8,539,663 B2 | 9/2013 | Wang et al. | |
| 8,595,913 B2 | 12/2013 | Knott et al. | |
| 8,752,261 B2 | 6/2014 | Van Sciver | |
| 8,752,265 B2 | 6/2014 | Wang | |
| 8,752,266 B2 | 6/2014 | Jow et al. | |
| 8,844,113 B2 | 9/2014 | Wang | |
| 8,904,619 B2 | 12/2014 | Low et al. | |
| 8,961,848 B2 * | 2/2015 | Roberts | B29C 66/92445 |
| | | | 264/249 |
| 9,032,607 B2 | 5/2015 | Jow et al. | |
| 9,155,870 B2 | 10/2015 | Wang | |
| 9,757,897 B2 | 9/2017 | Low et al. | |
| 9,937,068 B2 | 4/2018 | Vial et al. | |
| 10,059,034 B2 * | 8/2018 | Roberts | B29C 66/532 |
| 11,376,762 B2 * | 7/2022 | Roberts | B29C 66/92445 |
| 2002/0143382 A1 | 10/2002 | Hijlkema et al. | |
| 2004/0078953 A1 | 4/2004 | Spilka | |
| 2004/0106973 A1 | 6/2004 | Johnson | |
| 2004/0138731 A1 | 7/2004 | Johnson | |
| 2005/0119720 A1 | 6/2005 | Gale et al. | |
| 2005/0143752 A1 | 6/2005 | Schwager et al. | |
| 2006/0047336 A1 | 3/2006 | Gale et al. | |
| 2006/0100694 A1 | 5/2006 | Globerman | |
| 2007/0006441 A1 | 1/2007 | McNiven et al. | |
| 2007/0204455 A1 | 9/2007 | Knott et al. | |
| 2007/0271763 A1 | 11/2007 | Huang et al. | |
| 2007/0282433 A1 | 12/2007 | Limon et al. | |
| 2007/0289117 A1 | 12/2007 | Huang et al. | |
| 2008/0016668 A1 | 1/2008 | Huang et al. | |
| 2008/0033523 A1 | 2/2008 | Gale et al. | |
| 2008/0033524 A1 | 2/2008 | Gale | |
| 2008/0147164 A1 | 6/2008 | Gale et al. | |
| 2008/0275537 A1 | 11/2008 | Limon | |
| 2009/0001633 A1 | 1/2009 | Limon et al. | |
| 2009/0088829 A1 | 4/2009 | Wang et al. | |
| 2009/0105800 A1 | 4/2009 | Sabaria | |
| 2010/0004735 A1 | 1/2010 | Yang et al. | |
| 2010/0025894 A1 | 2/2010 | Kleiner et al. | |
| 2010/0063571 A1 | 3/2010 | Roach et al. | |
| 2010/0323091 A1 * | 12/2010 | Castro | A61F 2/915 |
| | | | 427/2.24 |
| 2011/0270383 A1 * | 11/2011 | Jow | A61F 2/958 |
| | | | 623/1.16 |
| 2011/0271513 A1 * | 11/2011 | Wang | A61F 2/82 |
| | | | 29/505 |
| 2012/0010693 A1 | 1/2012 | Van Sciver | |
| 2012/0042501 A1 | 2/2012 | Wang et al. | |
| 2012/0079706 A1 | 4/2012 | Knott et al. | |
| 2012/0285609 A1 | 11/2012 | Wang | |
| 2012/0316635 A1 | 12/2012 | Jow et al. | |
| 2014/0033506 A1 | 2/2014 | Jow et al. | |

FOREIGN PATENT DOCUMENTS

| | | |
|---|---|---|
| EP | 1 226 798 | 7/2002 |
| EP | 1 295 570 | 3/2003 |
| EP | 2 029 052 | 3/2009 |
| JP | 2008-538940 | 11/2008 |
| JP | 2009-540928 | 11/2009 |
| JP | 2009-542263 | 12/2009 |
| JP | 2010-525903 | 7/2010 |
| JP | 2010-540091 | 12/2010 |
| WO | WO 99/55406 | 11/1999 |
| WO | WO 02/102283 | 12/2002 |
| WO | WO 2005/053937 | 6/2005 |
| WO | WO 2006/110861 | 10/2006 |
| WO | WO 2006/117016 | 11/2006 |
| WO | WO 2007/116305 | 10/2007 |
| WO | WO 2007/146354 | 12/2007 |
| WO | WO 2007/149464 | 12/2007 |
| WO | WO 2008/033621 | 3/2008 |
| WO | WO 2008/137821 | 11/2008 |
| WO | WO 2009/045764 | 4/2009 |
| WO | WO 2010/151497 | 12/2010 |

OTHER PUBLICATIONS

Office Action dated Apr. 9, 2015 in Chinese Patent Application No. 201280030038.2, 17 pages.
Office Action dated Dec. 23, 2015 in Chinese Patent Application No. 201280030038.2, 7 pages.
Office Action dated Feb. 23, 2016 in Japanese Patent Application No. 2014-506487, 7 pages.
Office Action dated Jun. 17, 2016 in Chinese Patent Application No. 201280030038.2, 11 pages.
Office Action dated Feb. 22, 2019 in Indian Patent Application No. 8604/CHENP/2013, 6 pages.

* cited by examiner

METHODS FOR INCREASING A RETENTION FORCE BETWEEN A POLYMERIC SCAFFOLD AND A DELIVERY BALLOON

CROSS-REFERENCE

This application is a continuation of application Ser. No. 16/102,384, filed on Aug. 13, 2018, which is a continuation of application Ser. No. 14/535,246, filed Nov. 6, 2014 (U.S. Pat. No. 10,059,034), which is a continuation of application Ser. No. 13/089,225, filed Apr. 18, 2011 (U.S. Pat. No. 8,961,848), all of which are incorporated herein by reference in their entirety.

BACKGROUND OF THE INVENTION

Field of the Invention

The present invention relates to drug-eluting medical devices; more particularly, this invention relates to processes for crimping a polymeric scaffold to a delivery balloon.

Background of the Invention

The art recognizes a variety of factors that affect a polymeric scaffold's ability to retain its structural integrity when subjected to external loadings, such as crimping and balloon expansion forces. These interactions are complex and the mechanisms of action not fully understood. According to the art, characteristics differentiating a polymeric, bio-absorbable scaffolding of the type expanded to a deployed state by plastic deformation from a similarly functioning metal stent are many and significant. Indeed, several of the accepted analytic or empirical methods/models used to predict the behavior of metallic stents tend to be unreliable, if not inappropriate, as methods/models for reliably and consistently predicting the highly non-linear behavior of a polymeric load-bearing portion of a balloon-expandable scaffold (hereinafter "scaffold"). The models are not generally capable of providing an acceptable degree of certainty required for purposes of implanting the scaffold within a body, or predicting/anticipating the empirical data.

Moreover, it is recognized that the state of the art in medical device-related balloon fabrication, e.g., non-compliant balloons for scaffold deployment and/or angioplasty, provide only limited information about how a polymeric material might behave when used to support a lumen within a living being via plastic deformation of a network of rings interconnected by struts. In short, methods devised to improve mechanical features of an inflated, thin-walled balloon structure, most analogous to mechanical properties of a pre-loaded membrane when the balloon is inflated and supporting a lumen, simply provides little, if any insight into the behavior of a deployed scaffold. One difference, for example, is the propensity for fracture or cracks to develop in a scaffold. The art recognizes the mechanical problem as too different to provide helpful insights, therefore, despite a shared similarity in class of material. At best, the balloon fabrication art provides only general guidance for one seeking to improve characteristics of a scaffold.

Polymer material considered for use as a scaffold, e.g. PLLA or PLGA, may be described, through comparison with a metallic material used to form a scaffold, in some of the following ways. A suitable polymer has a low strength to weight ratio, which means more material is needed to provide an equivalent mechanical property to that of a metal. Therefore, struts must be made thicker and wider to have the strength needed. The scaffolding also tends to be brittle or have limited fracture toughness. The anisotropic and rate-dependant inelastic properties (i.e., strength/stiffness of the material varies depending upon the rate at which the material is deformed) inherent in the material only compound this complexity in working with a polymer, particularly, bio-absorbable polymer such as PLLA or PLGA.

Processing steps performed on, design changes made to a metal stent that have not typically raised concerns for, or require careful attention to unanticipated changes in the average mechanical properties of the material, therefore, may not also apply to a scaffold due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after scaffold fabrication, e.g., crimping. As a consequence, a change to a fabrication process, post-fabrication process or even relatively minor changes to a scaffold pattern design must, generally speaking, be investigated more thoroughly than if a metallic material were used instead of the polymer. It follows, therefore, that when choosing among different scaffold designs for improvement thereof, there are far less inferences, theories, or systematic methods of discovery available, as a tool for steering one clear of unproductive paths, and towards more productive paths for improvement, than when making changes in a metal stent.

It is recognized, therefore, that, whereas inferences previously accepted in the art for stent validation or feasibility when an isotropic and ductile metallic material was used, such inferences would be inappropriate for a scaffold. A change in a scaffold pattern may affect, not only the stiffness or lumen coverage of the scaffold in its deployed state supporting a lumen, but also the propensity for fractures to develop when the scaffold is crimped or being deployed. This means that, in comparison to a metallic stent, there is generally no assumption that can be made as to whether a changed scaffold pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, and the material's ductile nature), which simplify the stent fabrication process, allow for inferences to be more easily drawn between a changed stent pattern and/or a processing step and the ability for the stent to be reliably manufactured with the new pattern and without defects when implanted within a living being.

A change in the pattern of the struts and rings of a scaffold that is plastically deformed, both when crimped to, and when later deployed by a balloon, unfortunately, is not as easy to predict as a metal stent. Indeed, it is recognized that unexpected problems may arise in scaffold fabrication steps as a result of a changed pattern that would not have necessitated any changes if the pattern was instead formed from a metal tube. In contrast to changes in a metallic stent pattern, a change in a scaffold pattern may necessitate other modifications in fabrication steps or post-fabrication processing, such as crimping and sterilization.

One problem frequently encountered with a scaffold for delivery to a site in a body using a balloon is reliably retaining the scaffold on the balloon as it passes through tortuous anatomy. If the scaffold is not held on the balloon with sufficient force, it can slip off of the balloon during transit to the target site. For a metallic stent, there are several approaches proposed for increasing the retention of the stent to a balloon during transit to the target site. However, methods proposed thus far for retaining the scaffold on a balloon are in need of improvement.

In one example of a method for crimping a metallic stent to a delivery balloon, the stent is placed in a crimper and the temperature elevated to facilitate greater compliance in the balloon material to allow material to extend between gaps in the stent struts. Additionally, balloon pressure is maintained while the stent is being crimped to increase stent retention to the balloon. After an initial pre-crimp, the stent is placed on the delivery balloon and allowed to slightly recoil under balloon pressure and while the stent has an elevated temperature. After this step, the stent is crimped onto the balloon while the balloon is pressurized. The stent is cycled to larger and smaller diameters. Additionally, balloon pressure may be supplied in bursts or held constant during these crimping steps. Further details of this process may be found in U.S. application Ser. No. 12/895,646 filed Sep. 30, 2010. This application shares a common inventor with the present application.

In light of the foregoing problems, there is a need for improving the retention of a scaffold on a balloon while avoiding adverse effects on the mechanical characteristics of the scaffold when the scaffold is fully deployed to support a lumen.

SUMMARY OF THE INVENTION

It has been found that the retention force of a crimped polymer scaffold on delivery balloon may be increased by a process that includes crimping the scaffold to the balloon while the balloon is pressurized; that is, the balloon is pressurized at the same time as the scaffold's diameter is being reduced by crimper blades. Additional features of the crimping process include heating the scaffold to a temperature close to, but below the glass transition temperature (TG) of the polymer material and applying balloon pressure during dwell periods (i.e., balloon pressure is applied when the scaffold diameter is held constant).

The process includes several crimping steps. Following each crimping step, a dwell period occurs in which balloon pressure is supplied to correct any misalignments in scaffold struts, and/or deter further misalignment in subsequent crimping steps. After one or more initial crimping steps, the partially-crimped scaffold is removed from the crimper head to check alignment on the balloon. This step is referred to as the final alignment, or check final alignment step in the disclosure. After checking alignment, the scaffold is returned to the crimper to perform the final crimp. The final diameter reduction is performed while the balloon is pressurized to urge balloon material between gaps in the scaffold struts. It was found that there was a significant increase in the retention or pull-off force of the crimped scaffold on the balloon when the balloon was pressurized during the final crimping step.

In one aspect of the invention a scaffold crimped while balloon pressure is applied produces at least a 0.5 lb increase in retention force over a scaffold crimped using the same process but without balloon pressure supplied during the final crimp step. The scaffold may be manufactured from a precursor expanded into a tube then cut into a scaffold. The material may be a polymer comprising PLLA or PLGA. The crimping temperature may be between 5 and 15 degrees below a lower value for the polymer's TG.

In another aspect of the invention, a scaffold is reduced in diameter by a factor of at least 2.5 when crimped and has a retention force of above 1.0 lb. The crimping process includes pressurizing the balloon after the scaffold diameter is reduced by about 50% from its pre-crimp diameter.

In another aspect of the invention, the balloon pressure during dwell periods prior to a final alignment is about twice the balloon pressure applied after final alignment.

According to another aspect of the disclosure, a first crimping amount occurs before removing the scaffold to check alignment and a second crimping amount occurs after alignment. Greater balloon material can be urged between scaffold struts when the scaffold has a larger diameter; however, when at larger diameters the scaffold tends to move about more over the balloon (it also becomes more difficult to make longitudinal adjustments to scaffold position with respect to balloon markers if balloon material is urged between scaffold struts at the time of the first crimping amount). According to this aspect of the invention, the first and second amount of crimping are selected, in part, to crimp the scaffold sufficiently to enable adjustment of scaffold alignment on the balloon to achieve final alignment so that it will not shift on the balloon while leaving sufficiently-sized gaps between struts so that balloon material may be urged into gaps during the final crimp to increase scaffold retention force. In one embodiment the scaffold is reduced in diameter by about 50%, and then removed to check alignment. Then the scaffold is crimped by an additional about 33% to arrive at a final crimped diameter. The tube forming the scaffold has a diameter at about a deployed size or greater than a deployed size in this embodiment. For scaffold formed from a tube having a diameter less than or greater than a deployed size, each having the same final crimp size, the about 50% reduction may be correspondingly less than 50% or greater than 50%, respectively.

According to one embodiment, the ratio of diameter reduction before final alignment to the diameter reduction after final alignment may be about 1.5. For example, the scaffold diameter may be reduced by 50% before final alignment, and then reduced by 33% after final alignment.

The amount of diameter reduction for a single crimping step may be limited to no more than a 40% reduction in diameter, to allow for stress relaxation in the polymer material. The amount of diameter reduction and rate optimal for a scaffold will generally depend on the material and proximity to TG of the scaffold temperature during crimping. For example, the diameter reductions for a process that has three crimping steps may be about 20%, 40% and 30% for a PLLA scaffold and crimping temperature of about 48 Deg. Celsius. The scaffold diameter may be initially reduced in size by 20%, followed by a dwell period, then the diameter is reduced in size by 38%, followed by a second dwell period, and then reduced to its final crimped diameter by reducing the diameter by an additional 33% where balloon pressure is supplied to increase scaffold retention during the final step. For these crimping percentages a 3.5 mm scaffold would be reduced in diameter size from 3.5 mm to 1.19 mm.

According to another aspect of the invention, a method for crimping a balloon-expanded scaffold to a balloon includes the steps of providing a tube comprising PLLA characterized by a glass transition temperature range having a lower limit of about TG-low; radially expanding the tube to increase its radial stiffness; forming the scaffold from the radially-expanded tube, including the steps of forming a circumferential series of closed cells having a W-shape and linear link struts connecting the W-shape cells; and crimping the scaffold to the balloon while the scaffold has a crimping temperature of between about 5 to 15 degrees below TG-low including maintaining a pressure in the balloon as the scaffold diameter is being reduced in size.

According to another aspect of the invention, a method for securing a scaffold to a balloon includes the steps of crimping the scaffold to the balloon while the scaffold has a temperature of between about TG and 15 degrees below TG, the scaffold being made from a polymer comprising PLLA or PLGA, the crimping step including the steps of (a) reducing the scaffold diameter from a starting size to a first size, (b) maintaining the first size for a first dwell period to allow for stress relaxation in the polymer, (c) reducing the scaffold diameter from the first size to a second size, (d) maintaining the second size for a second dwell period to allow for stress relaxation in the polymer while the balloon has a first pressure, (e) reducing the scaffold diameter from the second size to a third size, (f) maintaining the third size for a third dwell period to allow for stress relaxation in the polymer while the balloon has the first pressure, and (g) reducing the scaffold diameter from the third size to a fourth size, wherein the balloon has a second pressure while the scaffold diameter is being reduced from the third size to the fourth size.

The scope of the methods and apparatus of the invention also encompass processes that may be used to crimp a scaffold as substantially described in US Pub. No. 2010/0004735 and US Pub. No. 2008/0275537. The thickness of the tube from which the scaffold is formed may have a thickness of between 0.10 mm and 0.18 mm, and more narrowly at or about 0.152 mm. The scaffold may be made from PLLA. And the scaffold may be crimped to a PEBAX balloon.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

DETAILED DESCRIPTION OF EMBODIMENTS

Figure 1A:
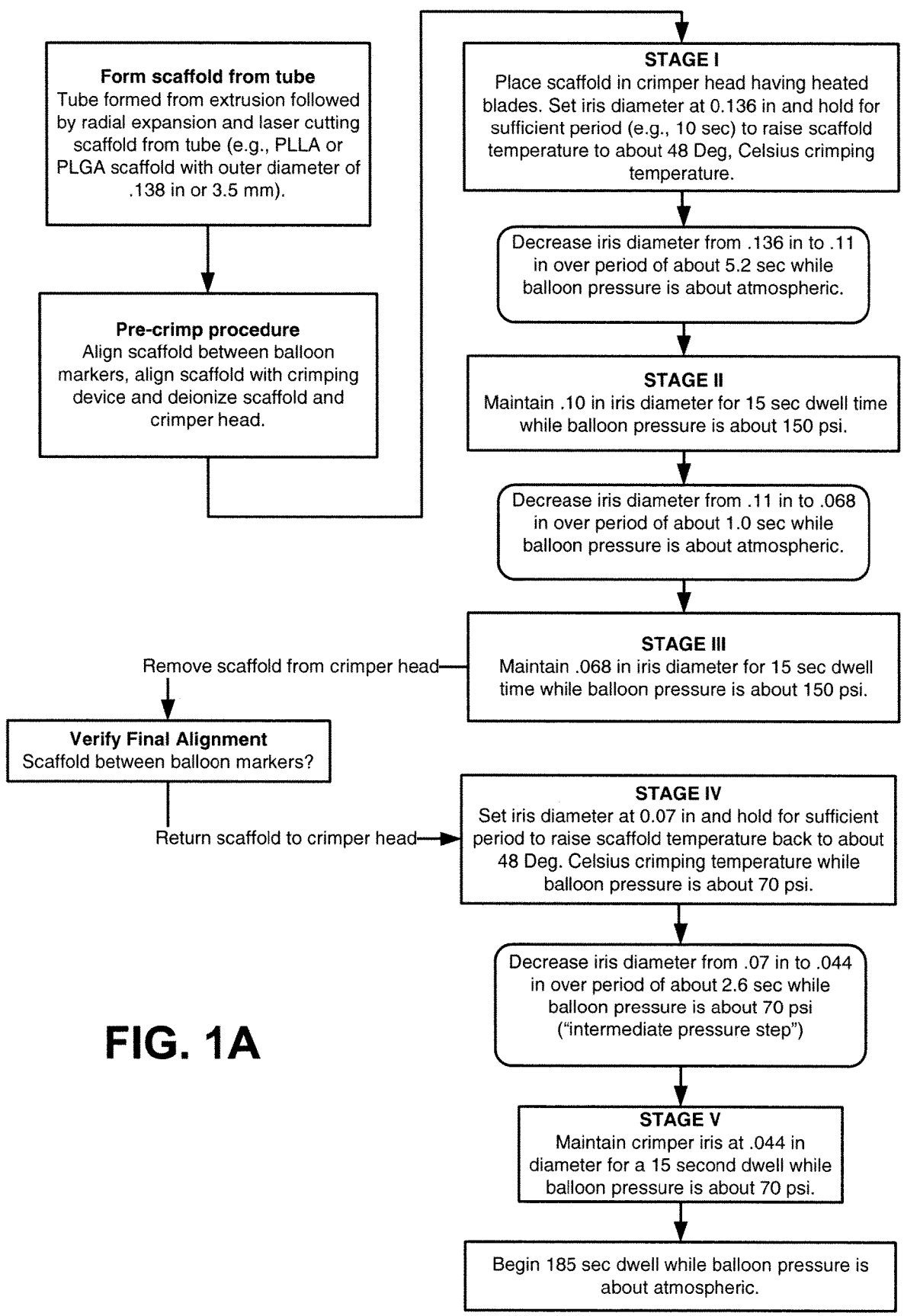
FIG. 1A shows a flow diagram for fabricating a scaffold and crimping the fabricated scaffold to a balloon according to the disclosure.

The "glass transition temperature," TG, is the temperature at which the amorphous domains of a polymer generally change from a brittle, vitreous state to a solid deformable or ductile state at atmospheric pressure. In other words, the TG corresponds to the temperature where the onset of noticeable segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. TG of a given polymer can be dependent on the heating rate and can be influenced by the thermal history of the polymer. Furthermore, the chemical structure of the polymer heavily influences the glass transition by affecting mobility.

Poly(lactide-co-glycolide) (PLGA) and Poly (L-lactide) (PLLA) are examples of a class of semi-crystalline polymers that may be used to form the scaffolds described herein. PLLA is a homopolymer and PLGA is a co-polymer. The percentage of glycolide (GA) in a scaffold constructed of PLGA may vary, which can influence the lower range of TG. For example, the percentage of GA in the matrix material may vary between 0-15%. For PLLA, the onset of glass transition occurs at about 55 degrees Celsius. With an increase of GA from about 0% to 15% the lower range for TG for PLGA can be correspondingly lower by about 5 degrees Celsius.

In one embodiment, a tube is formed by an extrusion of PLLA. The tube forming process described in US Pub. No. 2010/00025894 may be used to form this tube. The finished, solidified polymeric tube of PLLA may then be deformed in radial and axial directions by a blow molding process wherein deformation occurs progressively at a predetermined longitudinal speed along the longitudinal axis of the tube. For example, blow molding can be performed as described in U.S. Publication No. 2009/0001633. This biaxial deformation, after the tube is formed, can produce noticeable improvement in the mechanical properties of the scaffold structural members cut from the tube without this expansion. The degree of radial expansion that the polymer tube undergoes characterizes the degree of induced circumferential molecular or crystal orientation. In a preferred embodiment, the radial expansion ratio or RE ratio is about 450% of the starting tube's inner diameter and the axial expansion ratio or AE ratio is about 150% of the starting tube's length. The ratios RA and AE are defined in US Pub. No. 2010/00025894.

The above scaffold's outer diameter may be designated by where it is expected to be used, e.g., a specific location or area in the body. The outer diameter, however, is usually only an approximation of what will be needed during the procedure. For instance, there may be extensive calcification that breaks down once a therapeutic agent takes effect, which can cause the scaffold to dislodge in the vessel. Further, since a vessel wall cannot be assumed as circular in cross-section, and its actual size only an approximation, a physician can choose to over-extend the scaffold to ensure it stays in place. For this reason, it is preferred to use a tube with a diameter larger than the expected deployed diameter of the scaffold.

In one embodiment the ratio of deployed to fully crimped diameter is about 2.5. In this embodiment, the crimped diameter corresponds to an outer diameter that is only about 40% of the starting diameter. Hence, when deployed the drug eluting scaffold is expected to increase in size at least to about 2.5 times its crimped diameter size.

In one particular example, a scaffold is formed from a biaxially expanded tube having an outer diameter of 3.5 mm, which approximately corresponds to a deployed diameter (the scaffold may be safely expanded up to 4.0 mm within a lumen). The iris of the crimping mechanism reaches a diameter of 0.044 in, which is maintained for a 200 sec dwell period (i.e., scaffold held at 0.044 in outer diameter within crimping mechanism). When later removed from the crimper, the scaffold will recoil despite there being a restraining sheath placed over the scaffold immediately after the scaffold is removed from eth crimper. The scaffold and sheath are then subjected to radiation sterilization. At the point of use, i.e., at the point in time when a medical specialist removes the restraining sheath, the scaffold has an outer diameter of about 0.052 in (1.32 mm), or about 37% of the starting tube diameter of 3.5 mm. When in the crimping mechanism the scaffold reaches about 34% of the starting tube size.

As discussed earlier, fabrication of a scaffold presents challenges that are not present in metallic stents. One challenge, in particular, is the fabrication of a scaffold, which means the load bearing network of struts including connectors linking ring elements or members that provide the radial strength and stiffness needed to support a lumen. In particular, there exists an ongoing challenge in fabricating a scaffold that is capable of undergoing a significant degree of plastic deformation without loss of strength, e.g., cracks or fracture of struts. In the disclosed embodiments, a scaffold is capable of being deformed from a crimped diameter to at least 2.5 times the crimped diameter without significant loss of strength.

A problem encountered with fabrication of a scaffold for delivery to a site in a body using a balloon is the ability of the scaffold to be safely crimped to the balloon so that an adequate retention force is established between the scaffold and balloon. A "retention force" for a scaffold crimped to a balloon means the maximum force, applied to the scaffold along the direction of travel through a vessel that the scaffold-balloon is able to resist before dislodging the scaffold from the balloon. The retention force for a scaffold on a balloon is set by a crimping process, whereby the scaffold is plastically deformed onto the balloon surface to form a fit that resists dislodgment of the scaffold from the balloon. Factors affecting the retention of a scaffold on a balloon are many. They include the extent of surface-to-surface contact between the balloon and scaffold, the coefficient of friction of the balloon and scaffold surfaces, and the degree of protrusion or extension of balloon material between struts of the scaffold. As such, the pull off or retention force for a scaffold generally varies with its length. Therefore the shorter the scaffold the more likely it can become dislodged when the catheter is pushed through tortuous anatomy.

For a metal stent there are a wide variety of methods known for improving the retention force of a stent on a balloon via modification of one or more of the foregoing properties; however, many are not suitable or of limited usefulness for a scaffold, due to differences in mechanical characteristics of a scaffold verses a metal stent as discussed earlier. Most notable among these differences is brittleness of polymer material suitable for balloon-expanded scaffold fabrication, verses that of a metal stent, and the sensitivity of the polymer material to heat. Whereas a metal stent may be deformed sufficiently to obtain a desired retention force, the range of deformation available to a polymer scaffold, while avoiding cracking or fracture-related problems, by comparison, is quite limited. The application of heat has been shown as effective for increasing retention forces for metal stents. However, the heat levels used can cause detrimental effects to the polymer material since they tend to correspond to temperatures well within, or above the TG of the material. For this reason, known heat methods for increasing retention forces for metal stents tend to be viewed as inappropriate for increasing a retention force between a scaffold and balloon.

The invention addresses the unique challenges presented by a scaffold that needs to be retained on a balloon. These challenges are present for several reasons. First, there is less space available between struts in a crimped state, which prevents balloon material from extending between struts. As a result, there is less abutment or interference between struts and balloon material, which interference/abutment has previously been relied upon to increase the retention force of a metal stent on a balloon. This condition is a result of the need to fabricate wider and thicker struts for the scaffold, as compared to a metal stent, so as to provide adequate, deployed radial strength. Second, as indicated above, a polymer is more sensitive to temperature ranges that have previously been used to increase retention to a balloon. Heating of a scaffold to within, or above TG induces significant changes in the molecular orientation of the polymer material that result in loss of strength when the scaffold is plastically deformed to its deployed diameter.

The art has previously devised methods for retaining a scaffold on a delivery balloon in response to these challenges. In one example, the scaffold is crimped to the delivery balloon at a temperature well below the polymer's TG. Then the scaffold, disposed between ends of the balloon, is thermally insulated from the balloon's ends. The ends of the balloon are then heated to about 185 degrees Fahrenheit to expand the diameter of the balloon material at its ends. The expanded balloon ends form raised edges abutting the scaffold ends to resist dislodgment of the scaffold from the balloon. In one example, this process provided a retention force of about 0.35 lb. for a Poly (L-lactide) (PLLA) scaffold crimped to a polymide-polyether block co-polymer (PEBAX) balloon. An example of this process is disclosed in U.S. Pat. No. 6,666,880.

U.S. patent application Ser. No. 12/772,116 filed Apr. 30, 2010 ("'116 application) discusses a study that was conducted to investigate the effects on retention forces for crimped scaffolds. Principally, this study identified a temperature range relative to a TG of the scaffold material that improved retention forces without detrimentally affecting scaffold mechanical properties when deployed to support a vessel. For PLLA it was found that modifying the pressure and hold time of the scaffold for crimping temperatures of between 40° and 55° C. improved the scaffold retention, with about 45-51° C. and 48° C. being preferred temperatures for a PLLA scaffold. Additionally, the '116 application found that retention forces could be improved if the scaffold were crimped down to an intermediate diameter and then the balloon is deflated then re-inflated, followed by crimping the scaffold down to a final crimp diameter. The '116 application also contemplates similar results for PLGA, if TG for this material is taken into consideration and assuming other characteristics of the process and scaffold pattern. For PLGA having % GA of about 5% the temperature ranges for crimping may be between about 46 to 53 degrees Celsius. For PLGA having % GA of about 15% the temperature ranges for crimping are about 43 to 50 degrees Celsius.

When the scaffold is crimped to a balloon while being heated to temperatures well within the range of TG for the scaffold polymer, there is a greater tendency for polymer chain re-alignment to occur that will result in loss of strength when the scaffold is later deployed. Unacceptable crack formation (either in the number or extent of cracks), voids or outright fracture was observed in subsequent testing. If the crimping temperature is raised too high relative to the TG of the polymer, the memory of the matrix material at the starting tubing diameter is being removed, or reformed as the scaffold is deformed. As a consequence, when the scaffold is later expanded under physiological conditions, e.g., body temperature; it becomes more susceptible to crack formation due to its brittle properties at body temperatures and lack of chain alignment from its starting diameter. Retention force and scaffold integrity when crimped to the balloon generally improves at higher temperatures, however, the scaffold loses its structural integrity when later deployed if the temperature is raised too high, e.g., above TG. On the other hand, when the scaffold is heated to temperatures below about 15 degrees Celsius of the glass transition temperature, or not heated at all, there is no noticeable improvement in scaffold retention. It was found that the most effective range was between about 15 degrees below and up to about TG.

The '116 application explains that the above and related unexpected results may be explained in the following manner. When a polymer scaffold is crimped at a temperature slightly below its TG (e.g., from 5 to 15 degrees Celsius below TG), there are very short chains of the matrix material that are able to freely move to assist in the deformation of the scaffold without exceeding material stress limits. At the same time, the longer chains of the matrix substantially maintain their alignment, and, thus, stay intact without losing their orientation set when the starting tube was expanded. By doing so, the scaffold may be crimped down to a diameter for good scaffold retention, while the orientation of a majority of polymer chains would be the same to ensure desirable strength and fracture toughness in the final product, i.e., when the scaffold is deployed to support a vessel.

FIG. 1 of the '116 application shows a flow for a crimping process for a 3.0 mm (0.118 in) scaffold that is crimped to a final crimp diameter of 0.044 in. The diameter reduction from 0.118 in to 0.044 in includes three intermediate crimping diameters of 0.083 in, 0.063 in and 0.07 in, following a "pre-crimp" procedure in which the PLLA scaffold temperature is raised to a temperature of about 48° C. When the scaffold has attained the intermediate crimp diameters, the crimper jaws are held at the crimping diameter for a dwell period of 30 sec, 15 sec and 10 sec, respectively. After the final crimp diameter has been obtained, the crimp jaws are held at the final crimp diameter for about 200 sec. The delivery balloon, i.e., a PEBAX balloon, is inflated to a pressure of 17 psi for the dwell period 30, 15 and 10 second dwell periods. The dwell periods for the intermediate crimping stages are included in the process to allow for stress relaxation in the polymer material before decreasing the scaffold diameter further. Before the crimper iris is reduced by actuation of the crimper jaws, the balloon is deflated. Thus, in a preferred embodiment of the '116 application whenever the scaffold diameter is decreased, the balloon is not inflated.

Notwithstanding improved results in stent retention when practicing inventions described in the '116 application, it is desirable to further increase a scaffold retention force. For example, for a coronary scaffold it is desirable to have a balloon-scaffold retention force (i.e., force required to pull scaffold off balloon) of at least 0.7 lbs and preferably over 1.0 lbs. According to the disclosure, methods of the invention are expected to increase the retention force on an 18 mm length, 3.5 mm pre-crimp diameter scaffold by at least 0.5 lbs over the process used to produce the data in the '116 application.

Figure 1B:
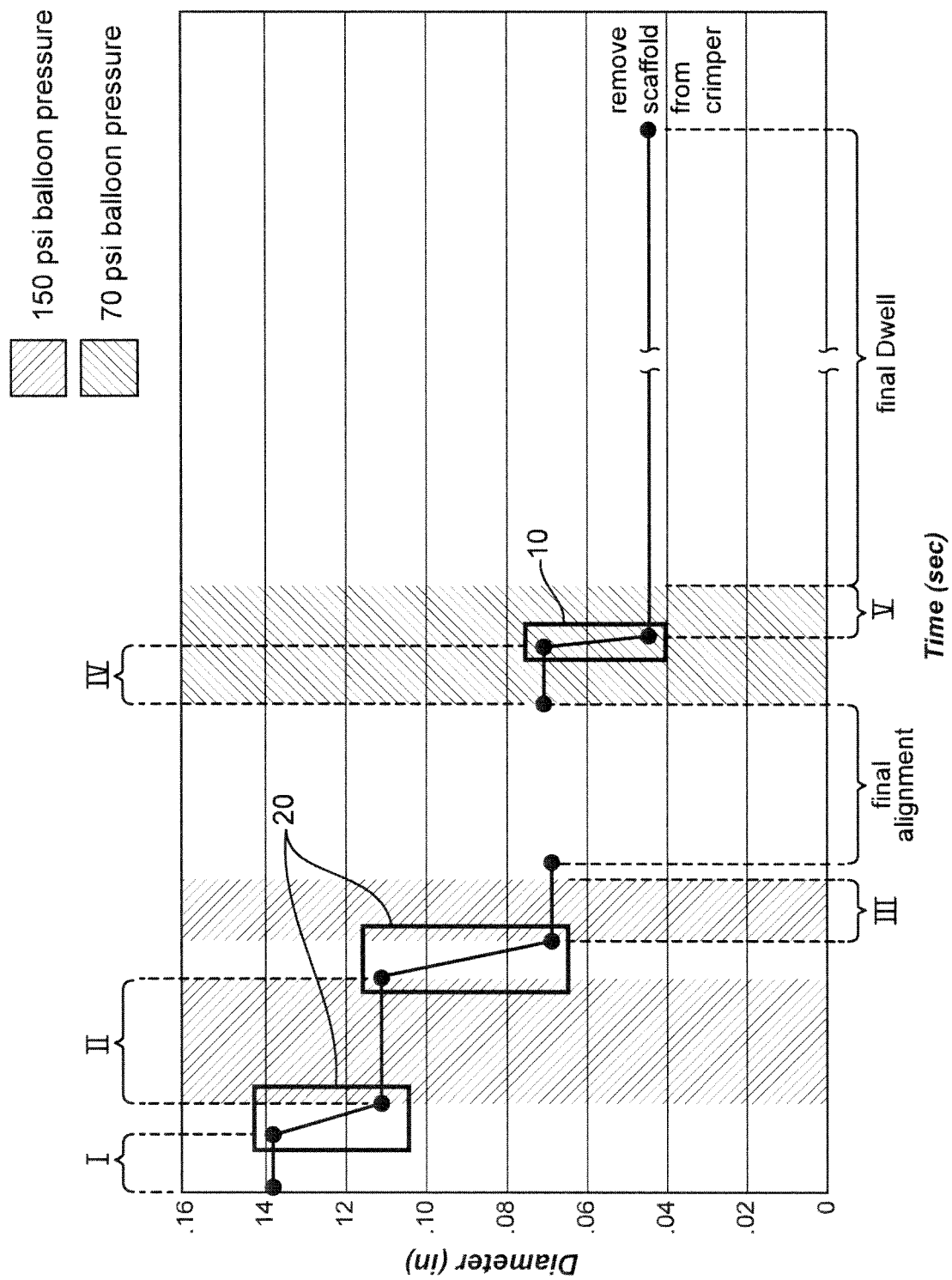
FIG. 1B shows the crimping process portion of FIG. 1A in graphical form, plotting scaffold diameter vs. time and indicating the balloon pressure supplied during steps of the crimping process.

Referring to FIGS. 1A-1B there is a flow process and graph, respectively, of a crimping method for a 3.5 mm diameter and 18 mm length scaffold. The method is discussed herein as a series of five "stages" with diameter reduction steps between stages. Each "stage" refers to a period where the crimper jaws are maintained at a constant diameter for a dwell period. The scaffold diameter is constant during these periods.

For the stages preceding the "final alignment" or "verify final alignment" step in FIGS. 1A-1B, where the scaffold and balloon are removed from the crimper to check alignment, the balloon is inflated to minimize further out of plane, or irregular movement or twisting of struts initiated in preceding crimping steps during subsequent crimping steps. Some of the advantages of inflating a balloon during these dwell periods to achieve this result are explained in U.S. application Ser. No. 12/861,719 filed Aug. 23, 2010.

As mentioned earlier, a polymer scaffold, and in particular a misaligned polymer scaffold is more susceptible to damage within a crimper than a corresponding metal stent. A polymer scaffold that has even a "slight" misalignment within the crimper has a far greater chance of becoming damaged than a metal stent. Of course, the need to avoid twisting or bending in struts of metal stents when in a crimper is known. However, unlike metal stents, which are far more tolerant of local irregular or non-uniform forces acting on struts through blade edges, polymer struts are more easily distorted when the crimping forces are non-uniformly applied. Due to the proximity of struts to each other (as required since thicker and wider struts are needed to provide equivalent stiffness to a metal stent and there is sometimes a greater diameter reduction needed during crimping), there is a greater chance of abutting struts which leads to out of plane twisting and overlapping scaffold structure in the crimped state. The effects of irregular or non-uniform crimping forces on a polymer scaffold are therefore more severe than in the case of a metal stent. The differences are most clearly evident in the instances of cracking and/or fracture in deployed polymer scaffolds that show irregular twisting or bending.

More local support for individual struts during the dwell periods is believed to correct for struts predisposed to twist or overlap with adjacent struts (a strut predisposed to twist or overlap with other struts refers to a strut that was previously slightly bent or twisted out of plane when the scaffold was at a larger diameter). In essence, balloon pressure during the dwell periods is believed to apply a beneficial correcting force on the luminal side of struts, which can serve to limit a strut's potential to overlap or twist further as crimper blades are applied in subsequent steps.

When crimped down from a larger diameter (e.g., from 0.136 to 0.11 in in FIG. 1A), there is little stabilizing support available for the scaffold since its diameter is much larger than the deflated balloon upon which the scaffold sits. As such, any initial non-uniform applied crimping force, or misalignment, e.g., due to a residual static charge on the polymer surface, can initiate irregular bending that becomes more pronounced when the scaffold diameter is reduced further. Friction between the blades and the scaffold surface, or residual static charge or static charge buildup induced by sliding polymer surfaces are also suspect causes of this irregular deformation of the scaffold. When the balloon is inflated to support the scaffold from the interior during dwell periods, the irregular bending and twisting of struts seen at the final crimp diameter (when the scaffold is removed from the crimper) were reduced substantially. The scaffold was more able to maintain a proper orientation with respect to the crimper axis.

Referring again to FIG. 1, the scaffold is partially crimped, then removed from the crimper to check its alignment on the balloon (Stages I, II, III as the dwell periods). The scaffold is then returned to the crimper to perform final crimp steps, e.g., Stage IV, reduce to 0.044 in, then dwell Stage V. During these final steps the balloon is approximately at a constant pressure. Unlike the earlier crimping steps, the balloon is pressurized when the scaffold is crimped to the final diameter. The presence of balloon pressure during the final crimp (the "intermediate pressure" step), as compared to the same process without the "intermediate pressure" step, i.e., about atmospheric balloon pressure for the final crimp, greatly increased the retention force of the scaffold to the balloon. Stated differently, the retention force of scaffold to balloon was much higher when the balloon is pressurized during the final crimp, or diameter reduction step.

It is believed that the greatly increased retention force was achieved because the balloon material opposing gaps in scaffold struts during the final crimp tended to extend in-between gaps more often as the scaffold was crimped due to the opposing balloon pressure applied to the balloon material. Without this pressure, the balloon material tended to deflect away from the gaps as the size of the gaps narrowed during the final crimp. Essentially, the balloon pressure forced more balloon material into gaps—rather than deflect the material away from the gaps—when the diameter is being reduced in size.

It should be noted that there was concern over whether the "intermediate pressure" step would cause balloon damage for balloon pressure applied in an amount that would make a difference in scaffold retention. The gaps between scaffold struts for a scaffold having significant diameter reductions and relatively thick struts are narrower than for struts of a metal stent. Forcing balloon material into narrower spaces gave rise to concerns that balloon material would be excessively pinched between struts, thereby causing damage to the balloon. In a preferred embodiment the pressure applied during the earlier dwell periods (Stages I, II and III) is about twice that applied during the final crimp steps (150 psi and 70 psi, respectively), as shown in FIGS. 1A-1B. This ratio of balloon pressure was found to produce good results, despite the previous concerns. It is contemplated that other pressure ratios, or increased pressure values may improve results. To the inventors' surprise, however, a relatively modest amount of pressure applied during the intermediate pressure step can produce significant improvement in scaffold retention, so that the risk of damaging a balloon and/or scaffold is reduced.

In other embodiments balloon pressure may be applied in bursts, rather than set at a constant level, during the intermediate pressure step. Further, there may be benefits to using balloon pressure during the prior partial crimp steps. Since the scaffold is re-aligned following the earlier crimp steps, the benefits of using balloon pressure during earlier crimping steps are not so much believed to lay in increased retention. Rather, balloon pressure may help avoid irregular twisting or bending in scaffold struts (for the reasons discussed above) as the scaffold diameter is being reduced.

EXAMPLES

Further details of the FIG. 1A flow process for a 3.5 mm scaffold manufacture and crimping to a delivery balloon will now be discussed. FIG. 1B illustrates in graphical form the crimping portion of the FIG. 1A flow—a graph of scaffold diameter verses time with a balloon pressure of 150 psi or 70 psi applied during the dwell periods and the intermediate pressure step (i.e., crimping between Stage IV and Stage V). The scaffold was crimped using a crimper having film-sheets disposed between the metal crimper blades and the scaffold. This particular type of crimper is discussed in greater detail below.

As discussed above, the scaffold is formed from a PLLA or PLGA precursor, including a biaxial expansion of the precursor to form a tube, followed by laser cutting the scaffold from the tube. Next, a pre-crimp procedure is performed, which includes placing the scaffold between the balloon markers and aligning the scaffold with the iris of the crimper. Using an anti-static air gun, both the scaffold and interior of the iris chamber are deionized. The deionization step was found necessary to reduce misalignments of the scaffold resulting from a static charge buildup caused by sliding contact between polymer surfaces, as explained in more detail in U.S. application Ser. No. 12/776,317 filed May 7, 2010.

Stacie 1: The scaffold (supported on the balloon of the balloon-catheter) is placed within the crimp head. The crimping temperature is obtained by heating the crimper jaws to an appropriate temperature and then bringing the jaws into thermal contact with the scaffold. The crimper jaws are set to 0.136 in and maintained in this position for about 10 seconds to allow the scaffold temperature to increase to a crimping temperature that is near to, but below the TG of the scaffold material (e.g., the crimping temperature for a PLLA scaffold of FIG. 1 is 48+/−3° C.). More generally, the scaffold temperature may be between 5 and 15 degrees Celsius below TG for the polymer material. Whenever the scaffold is within the crimper head its temperature is at, or rose to the crimping temperature (e.g., 48+/−3° C.) for the crimping process described in FIGS. 1A-1B.

After the scaffold reaches the crimping temperature, the iris of the crimper closes to reduce the scaffold diameter from 0.136 in (3.5 mm) to about 0.11 in, or about a 20% diameter reduction. During this diameter reduction step (Stage I→Stage II) the balloon pressure is maintained at about atmospheric temperature. The about 20% reduction in diameter occurs over a period of about 5.2 seconds. As compared to subsequent diameter reduction steps, this diameter reduction is performed more slowly because strut angles are at their widest. It was found that a slow rate of diameter reduction can significantly improve yield, in terms of more uniformity of compression in the scaffold structure; that is, to enable the scaffold structure to compress more evenly, without irregular bending or twisting of strut and/or link structure. Further details on this aspect of the crimping process are described in U.S. application Ser. No. 12/861,719 filed Aug. 23, 2010.

Stage II: The crimper jaws are held at the 0.11 in diameter, the balloon is inflated to a pressure of 150 psi, and the scaffold and balloon are maintained in this configuration for a 30 second dwell period at the crimping temperature. As explained earlier, the balloon is inflated to 150 psi to help with stabilizing the scaffold structure and correcting for any mis-alignment, or twisting of struts that might have occurred when the iris diameter was being reduced in size.

After the 30 second dwell period is complete, the balloon pressure is returned to about atmospheric pressure and the crimper iris is moved from 0.11 in to 0.068 in or about a 38% diameter reduction. During this second diameter reduction or crimp step (Stage II→Stage III) the balloon pressure is maintained at about ambient temperature. This about 38% reduction in diameter occurs over a period of 1.0 second. The about 50% diameter reduction was found to achieve an acceptable balance between balloon-scaffold engagement while retaining an ability to re-align the scaffold in a Final Alignment step). If the scaffold is crimped too tightly before Final Alignment, then it becomes difficult to re-position it between balloon markers. If crimped too loosely before Final Alignment, then the scaffold can shift again after Final Alignment. It will be appreciated that this balance also should take into consideration the available spacing between struts for balloon material.

Stage III: The crimper jaws are held at the 0.068 in diameter, the balloon is again inflated to a pressure of 150 psi, and the scaffold and balloon maintained in this configuration for a 15 second dwell period at the crimping temperature to correct or counter any twisting or misalignment that might have developed when the scaffold diameter was reduced by about an additional 38%.

Final alignment step: After the 15 second dwell period is complete, the scaffold and balloon are removed from the crimper to check the scaffold alignment on the balloon. This alignment involves a visual inspection and if necessary manual adjustment of the scaffold to place it between the balloon markers. Alternatively, alignment may be performed by an automated process, as explained in U.S. application Ser. No. 12/831,878 filed Jul. 7, 2010.

As mentioned earlier, the scaffold's starting or pre-crimp diameter is about equal to, or greater than the deployed diameter for the scaffold, which is between about 2.5 and 3.0 times its final crimped diameter. The expanded tube and pre-crimp scaffold diameter is 2.93 times the final-crimp size in the illustrated example. This difference in diameters between scaffold and balloon, coupled with the likelihood that crimper jaws will not apply a net-zero longitudinal force on the scaffold as the diameter is reduced, and/or that the scaffold will be slightly misaligned when it reaches the balloon surfaces, has lead to a need for re-aligning, or verifying alignment of the scaffold on the balloon; that is, checking to see that the scaffold is located between balloon markers.

The additional, time-consuming alignment step that interrupts the crimping process is typically not required for a metal stent, for two reasons. First, the starting diameter for a metal stent is much closer to the final diameter, which means the balloon-stent interaction that holds the stent in place happens relatively quickly. Second, for higher crimping rates used for metal stents, there is usually less ability for the stent to shift longitudinally over the balloon surface. Metal stents can be crimped at relatively high rates, whereas crimp rates for polymer scaffolds generally should be monitored and often times reduced (from metal crimp rates) because a polymer scaffold's structural integrity in its crimped and deployed states is affected by the crimp rate. While metals exhibit rate independent material behavior, polymers are viscoelastic and exhibit rate dependent material response. Polymers subjected to higher strain or displacement rates will experience higher stresses and exhibit less ductility.

After Stage III the scaffold's diameter has been reduced to about ½ of its starting diameter. It was observed that not until the scaffold diameter was reduced to about 50% of its pre-crimp diameter size was the scaffold-balloon interaction sufficient to prevent longitudinal shifting of the scaffold on the balloon when the scaffold was crimped down further. In the example of FIG. 1, therefore, the final-alignment step is performed once the scaffold reaches about 50% of its pre-crimp diameter. The Stage III diameter of 0.068 in places the scaffold relatively close to the deflated balloon to hold it in place, but not too tightly on the balloon so as to prevent re-alignment with respect to the balloon alignment markers. When the scaffold and balloon are removed from the crimper to check alignment, the scaffold recoils from the balloon (e.g., from about 0.068 in to about 0.075 in).

Stage IV: The scaffold and balloon are placed into the crimper. The jaws are closed to a diameter of 0.07 in and the balloon inflated to a pressure of 70 psi (the pressure used for the intermediate pressure step in this example). Thereafter the scaffold is crimped to its final crimp diameter of 0.044 in or about a 33% reduction in diameter over a period of about 2.6 seconds while balloon pressure is maintained at 70 psi. Before the final diameter reduction to 0.044 in commences, a dwell period of 10 seconds at the 70 psi balloon pressure is performed to allow time for the scaffold to return to the crimping temperature.

As illustrated in FIG. 1B, at the start of the Stage IV step the balloon pressure is set to 70 psi, and this setting is unchanged during the subsequent Stage IV dwell, the subsequent diameter reduction from 0.07 in to 0.044 in or about a 33% reduction ("intermediate pressure"), and the Stage V dwell. The pressure is not adjusted to maintain 70 psi; as such the balloon pressure is expected to change somewhat from 70 psi during the intermediate pressure step.

Stage V: After the scaffold has been reduced in diameter from 0.07 in to 0.044 in the balloon pressure is maintained at 70 psi for a period of about 15 seconds.

Following Stage V dwell period, the balloon pressure is returned to about atmospheric pressure and the crimper jaws are held at the final crimp diameter for a 185 second dwell period. During this final dwell period the degree of recoil in the scaffold is reduced. Immediately following the 185 second dwell the scaffold is removed and a retaining sheath is placed over the scaffold to reduce recoil.

Figure 2:
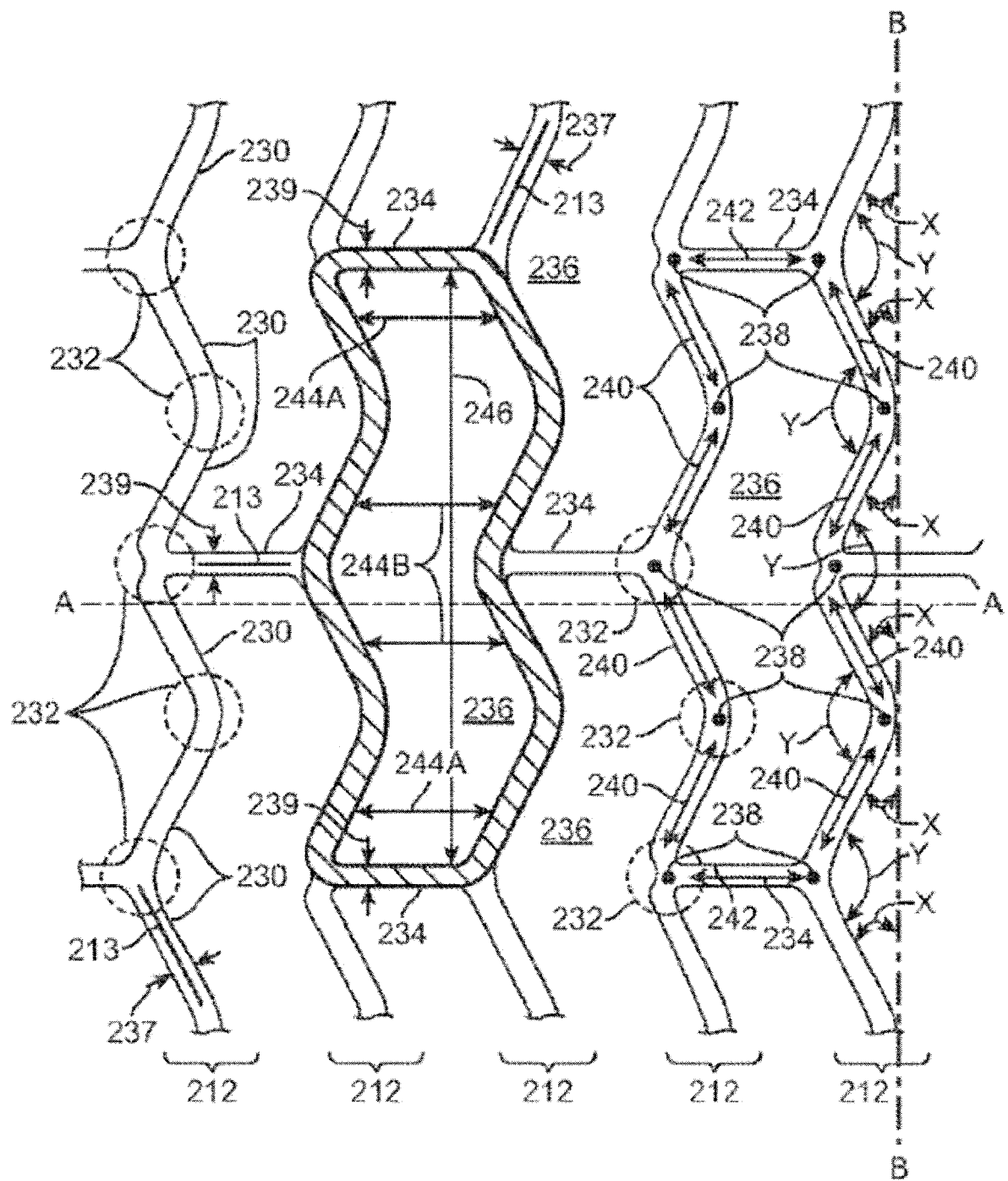
FIG. 2 is a planar view of a portion of a scaffold that was crimped to a balloon according to aspects of the disclosure. This view describes the scaffold pattern of the load-bearing structure of the scaffold that is crimped to a balloon according to the process of FIG. 1A-1B.

Trials were conducted to estimate the likely pull-off or retention force for a 3.5 mm×18 mm PLLA scaffold crimped to a 0.044 in final crimp diameter and crimped to a PEBAX balloon. The TABLE below shows results from these trials. The mean of the retention force for the scaffold for 9 trials using the process of FIGS. 1A-1B was significantly higher than the mean of the retention force for the "control case"— i.e., the same process as in FIGS. 1A-1B but without balloon pressure when the diameter was reduced from 0.07 in to 0.044 in the final crimping stages. The scaffolds used during these trials had substantially the same pattern as shown in FIG. 2. Statistics are shown for five Test cases.

| | Crimping process | Mean retention force (lb) | Standard deviation (lb) |
|---|---|---|---|
| FIG. 1A process | Test case 1 | 1.32 | 0.33 |
| | Test case 2 | 1.63 | 0.11 |
| | Test case 3 | 1.43 | 0.16 |
| | Test case 4 | 1.56 | 0.17 |
| | Test case 5 | 1.55 | 0.12 |
| FIG. 1A process without balloon pressure when diameter reduced from .07 to .044. | Control: | 0.70 | 0.10 |

The results above were unexpected, since it was previously not believed that a pressurization of the balloon during the final crimp by about ½ the pressure of prior dwell periods would make much of a difference in the retention force. The results demonstrate an about 30% to about 88% improvement in retention force over the "control" case.

As noted above, in a preferred embodiment a scaffold has the pattern described in U.S. application Ser. No. 12/447,758 (US 2010/0004735) to Yang & Jow, et al. Other examples of scaffold patterns suitable for PLLA are found in US 2008/0275537. FIG. 2 of US 2008/0275537 shows a detailed view of a strut pattern depicted in US 2010/0004735. The intermediate portion includes rings 212 with linear ring struts 230 and curved hinge elements 232. The ring struts 230 are connected to each other by hinge elements 232. The hinge elements 232 are adapted to flex, which allows the rings 212 to move from a non-deformed configuration to a deformed configuration. Line B-B lies on a reference plane perpendicular to the central axis 224 depicted in US 2010/0004735. When the rings 212 are in the non-deformed configuration, each ring strut 230 is oriented at a non-zero angle X relative to the reference plane. The non-zero angle X is between 20 degrees and 30 degrees, and more narrowly at or about 25 degrees. Also, the ring struts 230 are oriented at an interior angle Y relative to each other prior to crimping. The interior angle Y is between 120 degrees and 130 degrees, and more narrowly at or about 125 degrees. In combination with other factors such as radial expansion, having the interior angle be at least 120 degrees results in high hoop strength when the scaffold is deployed. Having the interior angle be less than 180 degrees allows the scaffold to be crimped while minimizing damage to the scaffold struts during crimping, and may also allow for expansion of the scaffold to a deployed diameter that is greater than its initial diameter prior to crimping. Link struts 234 connect the rings 212. The link struts 234 are oriented parallel or substantially parallel to a bore axis of the scaffold. The ring struts 230, hinge elements 232, and link struts 234 define a plurality of W-shape closed cells 236. The boundary or perimeter of one W-shape closed cell 236 is darkened in FIG. 2 for clarity. In FIG. 2, the W-shapes appear rotated 90 degrees counterclockwise. Each of the W-shape closed cells 236 is immediately surrounded by six other W-shape closed cells 236, meaning that the perimeter of each W-shape closed cell 236 merges with a portion of the perimeter of six other W-shape closed cells 236. Each W-shape closed cell 236 abuts or touches six other W-shape closed cells 236.

Referring to FIG. 2, the perimeter of each W-shape closed cell 236 includes eight of the ring struts 230, two of the link struts 234, and ten of the hinge elements 232. Four of the eight ring struts form a proximal side of the cell perimeter and the other four ring struts form a distal side of the cell perimeter. The opposing ring struts on the proximal and distal sides are parallel or substantially parallel to each other. Within each of the hinge elements 232 there is an intersection point 238 toward which the ring struts 230 and link struts 234 converge. There is an intersection point 238 adjacent each end of the ring struts 230 and link struts 234. Distances 240 between the intersection points adjacent the ends of rings struts 230 are the same or substantially the same for each ring strut 230 of the strut pattern. The distances 242 are the same or substantially the same for each link strut 234. The ring struts 230 have widths 237 that are uniform in dimension along the individual lengthwise axis 213 of the ring strut. The ring strut widths 234 are between 0.15 mm and 0.18 mm, and more narrowly at or about 0.165 mm. The link struts 234 have widths 239 that are also uniform in dimension along the individual lengthwise axis 213 of the link strut. The link strut widths 239 are between 0.11 mm and 0.14 mm, and more narrowly at or about 0.127 mm. The ring struts 230 and link struts 234 have the same or substantially the same thickness in the radial direction, which is between 0.10 mm and 0.18 mm, and more narrowly at or about 0.152 mm.

As shown in FIG. 2, the interior space of each W-shape closed cell 236 has an axial dimension 244 parallel to line A-A and a circumferential dimension 246 parallel to line B-B. The axial dimension 244 is constant or substantially constant with respect to circumferential position within each W-shape closed cell 236. That is, axial dimensions 244A adjacent the top and bottom ends of the cells 236 are the same or substantially the same as axial dimensions 244B further away from the ends. The axial and circumferential dimensions 244, 246 are the same among the W-shape closed cells 236.

It will be appreciated from FIG. 2 that the strut pattern for a scaffold that comprises linear ring struts 230 and linear link struts 234 formed from a radially expanded and axially extended polymer tube. The ring struts 230 define a plurality of rings 212 capable of moving from a non-deformed configuration to a deformed configuration. Each ring has a center point, and at least two of the center points define the scaffold central axis. The link struts 234 are oriented parallel or substantially parallel to the scaffold central axis. The link struts 234 connect the rings 212 together. The link struts 232 and the ring struts 230 defining W-shape closed cells 236. Each W-shaped cell 236 abuts other W-shaped cells. The ring struts 230 and hinge elements 232 on each ring 212 define a series of crests and troughs that alternate with each other. Each crest on each ring 212 is connected by one of the link struts 234 to another crest on an immediately adjacent ring, thereby forming an offset "brick" arrangement of the W-shaped cells.

An iris-type crimper from Machine Solutions, Inc (MSI) was used to crimp the scaffold according to FIGS. 1-2. The crimper includes three rolls arranged to position a clean sheet of non-stick material between crimping blades and the scaffold prior to crimping. The sheet is drawn from the backing sheet by a rotating mechanism (not shown) within the crimper head. A second sheet is dispensed from a mid roll. After crimping, the first and second (used) sheets are collected by a lower roll. Within the iris two sheets are passed between two blades on opposite sides of the positioned scaffold and balloon, and a tension is applied to gather up excess sheet material as the iris of the crimping assembly is reduced in size via the converging blades. For the crimping process of FIGS. 1A-1B the scaffold is crimped using this type of crimper. As explained in U.S. application Ser. No. 12/861,719 filed Aug. 23, 2010 it was found that the polymer sheets disposed between the scaffold and crimper blades help to reduce indentations in scaffold surfaces since the polymer sheets effectively make the blade surfaces more compliant.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:
1. A method for crimping a polymer scaffold to a balloon, comprising:
  using a crimping mechanism, crimping the scaffold to the balloon, including maintaining a pressure in the balloon as the scaffold diameter is being reduced in size, the crimping comprising

(a) reducing a scaffold diameter from a first diameter to a second diameter;

(b) reducing the scaffold diameter from the second diameter to a final diameter; and (c) interrupting the reduction of the scaffold diameter during step (a) and step (b) by performing a dwell break at step (a) and step (b) during which the scaffold diameter is held constant for a dwell period of time, wherein the dwell period at step (a) and the dwell period at step (b) is the same, and wherein the reduction of the scaffold diameter from the first diameter to the final diameter is by no more than 40% reduction in diameter before each of the dwell breaks, wherein the balloon has a first pressure during a stress relaxation period and a second pressure lower than the first pressure during step (b).

2. The method of claim 1, wherein the final diameter is at least 2.5 times less than the first diameter.

3. The method of claim 1, wherein the polymer scaffold is a stent made from a material comprising polylactide.

4. The method of claim 1, wherein the crimping is performed by a crimping apparatus and the method additionally comprises:

(a) removing the scaffold from the crimping apparatus during the reducing the scaffold diameter to adjust, if necessary, a position of the scaffold on the balloon to ensure accurate position of the scaffold on the balloon before the scaffold is crimped to the final diameter; and (b) placing the scaffold back into the crimping apparatus to resume the reducing the scaffold diameter to the final diameter.

5. The method of claim 4, wherein the adjustment of the position of the scaffold is made by aligning the scaffold between balloon markers.

6. The method of claim 1, wherein each dwell period of time is long enough to provide stress relaxation for the polymer scaffold.

7. The method of claim 6, wherein the each dwell period of time is less than 185 seconds.

8. The method of claim 1, wherein the balloon is inflated during the reducing the scaffold diameter from the first diameter to the final diameter.

\* \* \* \* \*